United States Patent [19]

Jones

[11] 3,958,939
[45] May 25, 1976

[54] METHOD FOR CLARIFICATION OF LIPEMIC SERUM
[75] Inventor: Alan Richardson Jones, Miami, Fla.
[73] Assignee: Coulter Electronics, Inc., Hialeah, Fla.
[22] Filed: Jan. 8, 1975
[21] Appl. No.: 539,401

[52] U.S. Cl. .............................. 23/230 B; 210/21; 210/DIG. 23; 260/112 B
[51] Int. Cl.² ........................................ G01N 33/16
[58] Field of Search ............ 23/230 B; 210/DIG. 23, 210/21; 260/412.8, 112 R, 112 B

[56] References Cited
UNITED STATES PATENTS

| | | | |
|---|---|---|---|
| 3,062,623 | 11/1962 | Schain | 23/230 B |
| 3,645,688 | 2/1972 | Smernoff | 23/230 B |
| 3,682,835 | 8/1972 | 230 B X | 23/230 BX |
| 3,706,660 | 12/1972 | Hagan et al. | 210/21 |
| 3,751,381 | 8/1973 | Megraw | 23/230 B X |
| 3,770,631 | 11/1973 | Fekete et al. | 260/112 B X |
| 3,791,791 | 2/1974 | Finkel et al. | 23/230 B |
| 3,839,314 | 10/1974 | Fekete et al. | 260/112 B |

OTHER PUBLICATIONS

Alaupovic et al., "Isolation & Characterization of Human Chyle Chylomicrons & Lipoproteins", Chemical Abstr., Vol. 70, 1969, 103036r.
Hatch et al., "Ultracentrifugal Isolation of Serum Chylomicron–Containing Fractions", Chemical Abstr., Vol. 67, 1967, 657c.
Pedini et al., "Separation of Serum Lipidic Fractions", Chemical Abstr., Vol. 71, 1969, 46644g.

*Primary Examiner*—Morris O. Wolk
*Assistant Examiner*—Arnold Turk
*Attorney, Agent, or Firm*—Silverman & Cass, Ltd.

[57] ABSTRACT

A method for the elimination of sample turbidity in blood serum samples where the turbidity is caused by the presence of chylomicrons, by forming an interface between the sample and a fat specific solvent, centrifuging the thus prepared unit and thereafter either decanting the solvent or withdrawing the cleared serum.

7 Claims, No Drawings

METHOD FOR CLARIFICATION OF LIPEMIC SERUM

BACKGROUND OF THE INVENTION

This invention relates generally to preparation of blood serum samples for biochemical analyses performed by photometric methods.

When performing biochemical analyses on blood serum or other body fluids, difficulties will be encountered time to time due to the presence of substances abnormally present in the serum, these substances producing direct absorption of light in a colorimetric measurement which is additive to the color intensity factors of the specific chemical reaction being observed.

Serum not only contains triglycerides which are held in solution conjugated with protein such as lipoprotein, principally beta-lipo-protein. As the proportion of protein in lipo-protein molecules decreases, the solubility of the molecule decreases. When the protein content reaches about 5 percent, the lipo-protein exists as finely emulsified droplets having a diameter greater than 0.5 microns and called chylomicra. These are visible and responsible for a serum turbidity called lipemia. Lipemia usually appears above a total serum lipid level of 500 to 1,000 milligrams per deciliter, but serum may remain optically clear at a liquid level as high as 4400 per milligrams per deciliter. Even clear serum or plasma may develop turbidity on standing, possibly as a result of aggregation of the lipo-protein molecules. The appearance of lipemia normally occurs after a meal containing fat. The sample turbidity due to chylomicrons, is common and is a source of error due to light scattering or light absorption by the fatty particles present in the specimen. This type of turbidity has been found to be extremely difficult to remove without subjecting the sample to a fat-extraction process which causes alteration or damage to other biochemical constituents which may be of interest.

It has been observed that when nonlipemic blood is subjected to a centrifugal field, a white zone appears at the air-plasma interface and when the centrifugal field is removed, the white zone disappears. The field strength range through which this phenomenon occurs has been found to be RCF 500 to 1000 where RCF is the relative centrifugal force. When lipemic blood was observed under the same conditions, the white zone was very pronounced. Further, the plasma between it and the red cell layer became quite clear. When the centrifugal field was removed, there was substantial redistribution of the white zone into the plasma although in the case of lipemic blood there remained a residual concentration within the white zone. Accordingly, it has been found that the removal of chylomicrons from lipemic blood by simple centrifugation is considerably difficult if not impossible.

Another suggestion for declarification would be the utilization of specific solvents added to the sample so as to extract the microscopic fat particles in known manner. A typical solvent would be ether mixed with the serum and then permitted to separate by gravity. As stated above, all the polar molecules in the serum as well as the chylomicrons would be exposed to the solvent action of the ether, hence such polar molecules as the sterols, e.g., cholesterol, would be affected. Thus, there would be a substantial disturbance of the relative concentration of the lipid-soluble components with deleterious results on the sample for further testing.

Accordingly, the invention provides a method for clarifying the lipemic blood serum samples having turbidity due to chylomicrons without subjecting the serum samples to the disadvantages encountered using either centrifugation alone or extraction with specific solvents.

BRIEF SUMMARY OF THE INVENTION

A method for clarification of chylomicron caused turbidity in lipemic blood serum samples, the method comprising the steps of forming an interface between the sample and a fat specific solvent and subjecting the interfaced liquids to a relative centrifugal field to drive the chylomicrons to the solvent layer, the chylomicrons being unable to redisperse into the serum once the relative centrifugal field is removed. The clear serum then is removed by decantation and/or probing.

DESCRIPTION OF THE PREFERRED EMBODIMENT

The invention herein provides a method of clarifying lipemic serum by centrifuging an aliquot thereof with a layer of fat specific solvent riding centripetally to it. The chylomicrons, having a lower specific gravity than the serum, will be driven upwards into and past the serum/solvent interface where they will be captured by the solvent. Then, when the centrifugal field is removed, it will not be possible for the chylomicrons to redisperse into the serum since in order to do so they would have to resume their particulate configuration in contrast to their solved configuration. The intermolecular forces operating in any solvent system are sufficiently large to prevent reversal of the solution into a dispersion form.

A wide variety of solvents may be utilized providing first that they are fat specific. These may include many known aliphatic, aromatic, halogenated or non-halogenated types, the limitation being that they are lipid solvents, immiscible with water and having a specific gravity less than that of blood serum. Blood serum has a specific gravity typically 1.030. Accordingly, ethyl ether, petroleum ether, and chloroform are appropriate solvents for use in practicing the method of the invention.

As an example of the method according to the invention, a few milliliters of lipemic blood serum are placed in a test tube and an equal volume of solvent such as ethyl ether is layered on top of the serum. By layering, we are applying the solvent to the serum in a manner so as not to mix the two but to define an interface between the two layers. It is essential that no attempt be made to mix or shake the solvent together with the blood serum. The test tube containing the two layers, one of lipemic serum and the other of the solvent, are placed in a centrifuge either of the fixed angle or swinging bucket type. The tubes are not stoppered. If necessary, one may provide a balance tube in the centrifuge containing water covered with a layer of solvent in order to provide constant evaporative loss at each end of the moment arm of the centrifuge.

The test tube and its contents then are centrifuged at approximately a relative centrifugal field (RCF) of 1500 for at least 5 minutes. Of course, the minimum amount of time required for centrifugation depends upon the extent of the lipemia being cleared. A 5-minute length of time is more than adequate for clearing even a severely turbid sample. While longer centrifugation may not produce any significant advantage, it is not believed that such longer centrifugation will do any harm to the material or the results obtained by observation of the material. The relative centrifugal field capable of being utilized has a minimum field strength of 1,000 with the upper end of the applicable range being limited only by the particular centrifuge utilized.

The centrifuge tube is removed from the centrifuge and both the ether and serum layers will be visually clear.

The solvent may be added to the serum or the serum to the solvent whichever is more convenient. However, it is inadvisable to shake the serum and solvent together. The serum and solvent may be separated by any convenient method depending upon whether it is desired to reclaim the solvent. Ordinarily, the solvent may be aspirated from above the serum using a fine glass probe connected to a vacuum source with a trap bottle. In the example concerned, the solvent has been aspirated from above the serum using a fine glass probe connected to a vacuum source by way of a trap bottle. It is possible to decant one liquid from the other, as well.

What is claimed and desired to secure by letters patent of the United States is:

1. A method for clarifying lipemic blood serum comprising the steps of forming an interface between a body of lipemic serum and a lipid-specific solvent having a specific gravity less than the serum and subjecting said interfaced liquids to a centrifugal field having a minimum field strength of 1,000 RCF for a predetermined duration while maintaining the integrity of said interface so that the solvent rides centripetally relative to the lipemic serum body, thereafter removing said interfaced liquids from said field and withdrawing one of the resulting solvent and serum layers without disturbing the other.

2. The method as claimed in claim 1 where the duration is not less than 5 minutes.

3. The method as claimed in claim 1 in which the solvent is a lipid-specific solvent selected from the group consisting of aliphatic, aromatic, halogenated and nonhalogenated, all being capable of receiving lipids in solution.

4. The method as claimed in claim 1 in which the lipid-specific solvent is selected from the group consisting of ethyl ether, petroleum ether and chloroform.

5. The method as claimed in claim 1 in which the lipid-specific solvent is ethyl ether.

6. The method as claimed in claim 1 where the field is 1500 RCF.

7. A method for clarification of chylomicron-caused turbidity in lipemic blood serum samples, the method comprising the steps of, forming an interface between the sample and a fat-specific solvent, subjecting the interfaced liquids to a centrifugal field having a minimum field strength of 1,000RCF to drive the chylomicrons to the solvent layer, removing the centrifugal field and thereafter removing the cleared serum by one of decantation or probed withdrawal, the chylomicrons being unable to redisperse into the serum once the centrifugal field is removed.

* * * * *

UNITED STATES PATENT AND TRADEMARK OFFICE
CERTIFICATE OF CORRECTION

PATENT NO. : 3,958,939
DATED : May 25, 1976
INVENTOR(S) : Alan Richardson Jones

It is certified that error appears in the above-identified patent and that said Letters Patent are hereby corrected as shown below:

Page 1, item 56, "230 B X" should read -- Louderback --.

Signed and Sealed this

Fourteenth Day of September 1976

[SEAL]

Attest:

RUTH C. MASON
*Attesting Officer*

C. MARSHALL DANN
*Commissioner of Patents and Trademarks*